United States Patent
Wu et al.

(10) Patent No.: US 10,555,909 B2
(45) Date of Patent: Feb. 11, 2020

(54) MICROENCAPSULATION OF B-ALANINE

(71) Applicant: INNOBIO CORPORATION LIMITED, Dalian, Liaoning (CN)

(72) Inventors: Wenzhong Wu, Liaoning (CN); Jianbin Chen, Liaoning (CN); Qian Li, Liaoning (CN); Xiangcheng Li, Liaoning (CN)

(73) Assignee: INNOBIO CORPORATION LIMITED, Dalian, Liaoning (CN)

( * ) Notice: Subject to any disclaimer, the term of this patent is extended or adjusted under 35 U.S.C. 154(b) by 0 days.

(21) Appl. No.: 16/067,340

(22) PCT Filed: Dec. 25, 2016

(86) PCT No.: PCT/CN2016/111997
§ 371 (c)(1),
(2) Date: Jun. 29, 2018

(87) PCT Pub. No.: WO2017/114339
PCT Pub. Date: Jul. 6, 2017

(65) Prior Publication Data
US 2019/0008786 A1    Jan. 10, 2019

(30) Foreign Application Priority Data
Dec. 30, 2015 (CN) .......................... 2015 1 1019193

(51) Int. Cl.
| | |
|---|---|
| A61K 47/14 | (2017.01) |
| A61K 9/14 | (2006.01) |
| A61K 31/197 | (2006.01) |
| A61K 9/50 | (2006.01) |
| A61K 9/00 | (2006.01) |

(52) U.S. Cl.
CPC .......... *A61K 9/5015* (2013.01); *A61K 9/0053* (2013.01); *A61K 9/5089* (2013.01); *A61K 31/197* (2013.01); *A61K 47/14* (2013.01)

(58) Field of Classification Search
CPC ...... A61K 31/197; A61K 9/50; A61K 9/5015; A61K 9/5089
See application file for complete search history.

(56) References Cited

U.S. PATENT DOCUMENTS

| | | | | |
|---|---|---|---|---|
| 5,126,151 A | * | 6/1992 | Bodor | A23G 4/066 426/305 |
| 8,329,207 B2 | * | 12/2012 | Harris | A61K 9/0095 424/439 |
| 2009/0220575 A1 | * | 9/2009 | Harris | A61K 9/0095 424/439 |

FOREIGN PATENT DOCUMENTS

| | | |
|---|---|---|
| CN | 101658244 A | 3/2010 |
| CN | 101744111 A | 6/2010 |
| CN | 102908337 A | 2/2013 |
| CN | 104258793 A | 1/2015 |
| CN | 105434402 A | 3/2016 |
| CN | 105663081 A | 6/2016 |
| DE | 202013104575 U1 | 1/2014 |
| JP | 04-305243 A | 10/1992 |
| JP | 2008542282 A | 11/2008 |
| JP | 2012523462 A | 10/2012 |
| JP | 2015518031 A | 6/2015 |
| WO | 2007073398 A2 | 6/2007 |

OTHER PUBLICATIONS

English translation provided by Google of CN105434402A published Mar. 30, 2016 (Year: 2016).*
Burdick, GA. (Fenoroli's Handbook of Flavor Ingredients 2001, CRC Press. p. 34). (Year: 2001).*
Liu et al. The Journal of Neuroscience. 2012;32(42):14532-14537 (Year: 2012).*
Gharsallaoui et al, "Applications of spray-drying in microencapsulation of food ingredients: An overview", Food Research International, vol. 40, No. 9, Nov. 2007, pp. 1107-1121.
European Patent Office, Office Action and Supplementary European Search Report for EP 16881128, dated Jul. 16, 2019.
Japanese Patent Office, Office Action for JP 2018534841A, dated Jul. 26, 2019.

* cited by examiner

*Primary Examiner* — Ernst V Arnold
(74) *Attorney, Agent, or Firm* — Novick, Kim & Lee, PLLC; Allen Xue

(57) ABSTRACT

Microencapsulation of β-alanine uses β-alanine as a core material and a mixture of a wall material and an additive as a release material. The additive comprises: a fatty acid-based saturated or unsaturated fatty acid glyceride containing 12-22 carbon atoms and a phospholipid. The fatty acid glyceride is a mono-fatty acid glyceride or a di-fatty acid glyceride, or a mixture formed by mixing the mono-fatty acid glyceride and the di-fatty acid glyceride at arbitrary proportions. The microencapsulation technique solves problems occurring with the use of β-alanine as a raw material, such as high moisture absorption tendency thereof, unpleasant smell and stinging accompanying administration of the same. The invention selects and combines the wall material and the additive to attain a balance between embedment and release with respect to a microencapsulated β-alanine product, and effectively optimizes release kinetics of the product, thereby enabling a stable release of the product, and realizing effective embedment and uniform release. Therefore, the microencapsulated β-alanine is applicable to the preparation of food, drugs, health-enhancing products and functional food.

11 Claims, No Drawings

MICROENCAPSULATION OF β-ALANINE

TECHNICAL FIELD

The present invention relates to a sustained-release microencapsulated β-alanine preparation and a preparation method.

BACKGROUND

β-alanine, L-histidine and methylated analogue thereof form dipeptide in a human body or animal body. The dipeptide generated from β-alanine and histidine comprises carnosine, anserine or balenine. The carnosine is the most abundant dipeptide in the muscle of the human body. The concentration of the β-alanine in the muscle is lower than that of the L-histidine. Therefore, the β-alanine may be the rate-limiting precursor for the carnosine synthesis. The existing studies have shown that the β-alanine can increase the carnosine concentration in the muscle, thereby increasing the muscle endurance and working ability, enhancing the muscle buffering capacity, reducing acidosis, increasing the muscle strength, and delaying fatigue. However, the intake of the β-alanine can produce paresthetic side effects, comprising burning, pricking or tingling sensation. Generally, pricking or tingling sensations can be produced in several minutes to several hours after the intake of the β-alanine. The side effects are caused by the increased blood concentration of the β-alanine, the microencapsulated β-alanine reduces the rate of the β-alanine entering the blood through the retained release of core materials and slows down the blood concentration increase of the β-alanine, thereby effectively reducing or eliminating adverse reactions and increasing compliance.

There are many methods for preparing sustained-release microcapsules, and the release rate of the preparation is determined by various factors such as the preparation method and sustained-release materials together. The commonly used methods for sustained-release microencapsulations comprise fluidized coating, wet granulation, spray condensation, etc. In the prior art, there are also many records applying the methods above to prepare the microencapsulated β-alanine preparation. Meanwhile, those skilled in the art have never stopped the optimization to the preparation method of the microencapsulated β-alanine. In the technical optimization to the microencapsulated β-alanine, adding a suitable wall material additive to the release material is an important means to improve the encapsulation quality and optimize the release behavior of the microcapsule. The inventor of the application has also actively explored selection and addition methods of additives in related studies. However, in the optimization to the release material of the microencapsulated β-alanine, it is still difficult to reconcile the contradiction between encapsulation strengthening and release promoting. The research priority of the inventor of the application is how to enable the microencapsulated β-alanine to have relatively high encapsulation efficiency while still retaining a satisfactory release behavior.

SUMMARY

An object of the present invention is to provide a microencapsulated β-alanine, the microencapsulated β-alanine uses β-alanine as a core material and a mixture of a wall material and an additive as a release material, wherein the additive comprises a fatty acid-based saturated or unsaturated fatty glyceride containing 12 to 22 carbon atoms and a phospholipid; and the fatty glyceride is a monoglyceride, a diglyceride, or a mixture thereof in any ratio.

Another object of the present invention is to provide a preparation method of the microencapsulated β-alanine above, and the method comprises a step of preparing release materials: melting the wall material firstly, then stirring at a hot-melting temperature, adding the additive and mixing evenly.

The present invention overcomes the inherent defects of the material β-alanine in application by the microencapsulated technology, and solves the problems of easy moisture absorption, bad smell and tingling sensation in administration of the β-alanine; and optimizes the encapsulation and release performances of the β-alanine through selecting and combining the wall material additives. On this basis, another aspect of the present invention further provides an application of the microencapsulated β-alanine to prepare food, drugs, health care products and functional food.

The present invention further provides a method of supplementing β-alanine but decreasing or not causing an abnormal sensation, which refers to orally administrating the microencapsulated β-alanine of the present invention or a composition containing the microencapsulated β-alanine of the present invention, wherein an oral administration dosage, based on the β-alanine, is 22.8 to 71.4 mg/Kg (body weight), and the microencapsulated β-alanine is administrated 1 to 2 times per day.

DETAILED DESCRIPTION

The present invention provides a microencapsulated β-alanine using β-alanine as a core material and a mixture of a wall material and an additive as a release material. The additive comprises a fatty acid-based saturated or unsaturated fatty glyceride containing 12 to 22 carbon atoms and a phospholipid; and the fatty glyceride is a monoglyceride, a diglyceride, or a mixture thereof in any ratio.

The fatty glyceride mentioned in the present invention is preferably selected from the fatty acid-based fatty glyceride containing 16 to 18 carbon atoms; more preferably selected from glyceryl hexadecanoate, glyceryl hexadecenoate, glyceryl octadecanoate, glycerol octadecenoate, glyceryl octadecadienoate and glyceryl octadecatrienoate; and particularly, preferably selected from glycerol monostearate and glycerol distearate, glycerol monolaurate and glycerol dilaurate, glycerol monooleate and glycerol dioleate. In a more specific embodiment, a dosage of the fatty glyceride is 0.2 to 5%, preferably 0.4 to 3%, and more preferably 0.5 to 1% of a mass of the wall material.

The phospholipid is the phospholipid extracted from vegetable oil, comprising concentrated phospholipid, powder phospholipid (deoiled phospholipid) and the phospholipid with modified structure. The adding of the phospholipid is possible to form a water soluble channel in a continuous coating layer, to as to be able to increase the dissolution of core material and increase the release rate. A dosage of the phospholipid in the present invention is 0.5 to 10%, preferably 1 to 6%, and more preferably 2 to 5% of a mass of the wall material. Soybean phospholipid or sunflower phospholipid is preferably used.

More preferably, a mass ratio of the fatty glyceride to the phospholipid is 1:50 to 10:1, preferably 1:15 to 3:1, and more preferably 1:5 to 1:2.

In another specific embodiment, the wall material in the present invention is selected from hydrogenated palm oil, hydrogenated soybean oil, hydrogenated sunflower oil, hydrogenated peanut oil, hydrogenated cottonseed oil, hydrogenated corn oil, stearic acid, beewax, carnauba wax or a mixture thereof in any ratio. The wall material is preferably selected from hydrogenated palm oil, hydrogenated soybean oil, hydrogenated sunflower oil, hydrogenated peanut oil, hydrogenated cottonseed oil, hydrogenated corn oil or a mixture thereof in any ratio. The wall material is more preferably selected from hydrogenated palm oil or a mixture formed by other oils. The wall material is most preferably selected from hydrogenated palm oil. Wherein, the above-mentioned any ratio shall be understood as that: in the formed mixture, the content of any one or multiple wall materials is possible to be zero.

In a preferred embodiment, the microencapsulated β-alanine according to the present invention uses β-alanine as the core material and hydrogenated palm oil as the wall material, at least the fatty glyceride and the phospholipid are added in the wall material as additives, the fatty glyceride is preferably selected from glycerol mono stearate and glycerol distearate, and the phospholipid is preferably selected from sunflower phospholipid or soybean phospholipid; wherein, a mass ratio of the hydrogenated palm oil to the β-alanine is 1:1 to 19, preferably 1:1.5 to 4, and more preferably 1:2 to 3; a dosage of the fatty glyceride is 0.2 to 5%, preferably 0.4 to 2%, and more preferably 0.5 to 1% of a mass of the wall material hydrogenated palm oil; a dosage of the phospholipid is 0.5 to 10%, preferably 1 to 6%, and more preferably 2 to 5% of the wall material hydrogenated palm oil.

One or more of the following constituents can further be selectively added in the microencapsulated β-alanine of the present invention according to the conventional dosage in the alt (1) Water soluble constituent, which can be, for example, but is not limited to glucose, lactose, maltooligosaccharide, polyethylene glycol, sodium carboxymethylcellulose and solid corn syrup.

(2) Surfactant used for solving the problem that a product made of non-water soluble fat or wax material usually floats on water, and increasing the water dispersibility of the product. The surfactant can be illustrated but is not limited to polysorbate 60, polysorbate 80 or sucrose fatty acid ester.

(3) Adhesive, which can be, for example, but is not limited to povidone, glycerinum, propylene glycol, polyglycerol fatty acid ester, soluable soybean polysaccharide and sodium carboxymethylcellulose.

(4) Suspending agent, which can be, for example, but is not limited to Arabic gum, gelatin, guar gum, xanthan gum, sodium alginate, hydroxypropyl methyl cellulose, methylcellulose, gellan gum and carrageenan.

(5) Diluent, which can be, for example, but is not limited to starch, maltooligosaccharide, maltodextrin and cane sugar.

(6) Stabilizer, which can be, for example, but is not limited to sodium lactate, sodium citrate, magnesium carbonate, sodium bicarbonate and microcrystalline cellulose.

(7) Flow aid, which can be, for example, but is not limited to silicon dioxide, corn starch and calcium silicate.

(8) Antioxidant, which can be, for example, but is not limited to vitamin E, vitamin C and the ramifications thereof.

Due to the proper selection of the additive promoting the encapsulation and release, the microencapsulated β-alanine of the present invention enables a surface amino acid content of the acquired microencapsulated β-alanine product to be less than 10%; and a release rate in a pH 6.8 phosphate buffer is no more than 50% in 1 h, and the microencapsulated β-alanine is completely released in 18 h. According to the common understanding in the art here, the complete release is 100±10% of the measurement value.

More specifically, the size of the microencapsulated β-alanine of the present invention is 100 to 1000 μm; and the mass percentage content of the β-alanine in the microencapsulated product is 50 to 95%;

Another aspect of the present invention discloses a preparation method of the microencapsulated β-alanine mentioned in the present invention above, and the method comprises a step of preparing release materials: melting the wall material firstly, then stirring at a hot-melting temperature, adding the additive and mixing evenly. The melting here refers to heating the wall materials in a solid state under a normal temperature to become a melted state according to the common understanding in the art. The required temperature can be set according to a melting point of specific wall material, and those skilled in the art can select and implement without doubt.

In a preferred embodiment, the preparation method of the microencapsulated β-alanine comprises a step of preparing release materials: melting the wall material, stirring at a hot-melting temperature, adding the additive and mixing evenly, cooling an acquired mixture to a temperature of 0 to 5° C., and using the mixture as the release material after being placed at 0 to 5° C. for at least 24 h. The temperature can be cooled by regular temperature control method to enable the environment temperature of the mixture to be in a required temperature scope. In a specific embodiment, the mixture acquired under the melting temperature is placed in 0 to 5° C. refrigerating fluid for more than 24 h.

On the basis that the core material and the release material are prepared, the microencapsulated coating method commonly used in the art can be used for preparing the microencapsulated preparation in the present invention.

A first specific embodiments is that the β-alanine using as the core material is dispersed in melted release material prepared by the method above, and then is atomized and cooled.

A second specific embodiment is that the release material prepared by the method above is melted, and the core material β-alanine is coated in a fluidized bed. More specifically, a top spraying or bottom spraying processes can be used for coating, wherein:

the top spraying process is that: an inlet air temperature is 45 to 73° C., an air volume is 20 to 50 m$^3$/h, the β-alanine is kept in a good fluidized state, an atomizing pressure is 0.1 to 0.3 Mpa, a flow speed is 3 to 20 ml/min, and in order to avoid adhesion, the flow speed needs to gradually increase to a proper level.

The bottom spraying process is that: an inlet air temperature is 45 to 73° C., an air volume is 20 to 50 m$^3$/h, a distance between a lower end of a draft tube and a distribution plate is adjusted, the β-alanine is kept in a good fluidized, an atomizing pressure is 0.1 to 0.3 MPa, a flow speed is 3 to 20 ml/min, and in order to avoid adhesion, the flow speed needs to gradually increase to a proper level.

A third specific embodiment is that the core material β-alanine and the melted release material are mixed in a homogenizer until the release material is evenly coated on the surface of the β-alanine, and then the release material is cooled. A further specific process can be described as follows: the release material and the β-alanine are placed in the homogenizer provided with a jacketed insulation system to be heated to 45 to 73° C. and stirred by 1000 to 2000 RPM rotate speed, the melted release material is evenly coated on the surface of the β-alanine with the stirring, the rotate speed is reduced and the temperature is lowered, and the melted release material is cooled and solidified.

The present invention conducts the collaborative optimization to the release rate and the encapsulation efficiency of the microencapsulated β-alanine product through the selection and ratio adjustment of the wall material and the additive. Therefore, the acquired product has satisfactory performance on the two aspects at the same time. Specifically, the adding of the fatty glyceride can promote the encapsulation promotion efficiency of the microencapsulated β-alanine in the present invention; moreover, the using of the phospholipid promotes the release of the core material in the microencapsulated β-alanine in the present invention; the fatty glyceride and the phospholipid are added according to the limited ratio of the present invention, then the relationship between the encapsulation and the release of the microencapsulated β-alanine product in the present invention is balanced, and release kinetics of the product is effectively optimized, so that the release of the product is stable, and effective encapsulation and sustained release with constant speed are realized.

The microencapsulated β-alanine preparation of the present invention can be used as a material that is further processed into dietary supplement in a form of tablet or capsule, or is made into food or functional food in a form of solid drink, energy bar or candy.

The following non-restrictive embodiments will further describe the present invention, which shall not be understood as limiting the present invention in any form, and the following method is used in the application to measure and evaluate the product without special statement.

In the present invention, a surface amino acid content is used to show the microencapsulation efficiency, the higher the surface amino acid content is, the lower the microencapsulation efficiency is, and the more the unencapsulated core materials are, the quicker the release is. The measurement method of the surface amino acid content according to the present invention comprises: 5 g microencapsulated product to be measured is added in a conical flask, 50 ml pure water is added, the filtering is conducted after shaking for 20 s, the washing is conducted once again, the filter liquor is combined, the pure water is removed by rotary evaporation, and a mass ratio of a dry weight of the residual solid to the microencapsulated product to be measured is a surface active ingredient content, which is represented by percentage.

Regarding to the measurement to the release rate in the present invention, the release rate experiment in 0.1N hydrochloric acid solution and pH6.8 phosphate buffer is conducted referring to USP<711>DISSOLUTIO and using Apparatus 2 with a rotate speed of 50 rpm by DELAYED-RELEASE DOSAGE FORMS method B.

The evaluation method of the tingling sensation in the present invention is that: a subject respectively administrates unsustained-release microencapsulated material containing a certain amount of β-alanine and sustained-release microencapsulated β-alanine. The time, intensity and duration of having the abnormal sensation are recorded. Intensity: 0 refers to having no sensation, 1 to 5 refer to have acceptable sensation (the intensity is gradually increased), and 6 to 10 refer to have unacceptable sensation (the degree is gradually strengthened).

First Embodiment (1) 600 g hydrogenated palm oil was heated and melted, and 600 g β-alanine was placed in a fluidized bed and coated by a top spraying process. An inlet air temperature of the fluidized bed was 73° C., an air volume was 20 m³/h, an atomizing pressure was 0.1 Mpa, a flow speed was 3 ml/min, a sustained-release microencapsulated β-alanine product B was acquired, a β-alanine content thereof was 50.0%, and parameter evaluation is as shown in Table 1.

(2) 933 g hydrogenated palm oil was heated and melted, and 1400 g β-alanine was placed into a fluidized bed and coated by a by a bottom spraying process. An inlet air temperature of the fluidized bed was 70° C., an air volume was 15 m³/h, an atomizing pressure was 0.1 Mpa, a flow speed was 10 ml/min, a sustained-release microencapsulated β-alanine product C was acquired, a β-alanine content thereof was 60.2%, and parameter evaluation is as shown in Table 1.

(3) 200 g hydrogenated palm oil was heated and melted, and 3800 g β-alanine was placed in a fluidized bed and coated by a top spraying process. An inlet air temperature of the fluidized bed was 66° C., an air volume was 17 m³/h, an atomizing pressure was 0.2 Mpa, a flow speed was 12 ml/min, a sustained-release microencapsulated β-alanine product D was acquired, a β-alanine content thereof was 95.0%, and parameter evaluation is as shown in Table 1.

TABLE 1

Size change of β-alanine before and after sustained-release microencapsulation

| | β-alanine | Size distribution | | |
|---|---|---|---|---|
| Product No. | mass content | 300-450 μm | 450-900 μm | 900-1000 μm |
| A | 99.7% | 0 | 43.7% | 56.3% |
| B | 50.0% | 7.5% | 47.3% | 45.2% |
| C | 60.2% | 5.0% | 45.8% | 49.2% |
| D | 95.0% | 2.1% | 44.9% | 53.0% |

In Table 1, a product A is a non-microencapsulated β-alanine, and the products B, C and D are microencapsulated β-alanine products.

The tingling sensation after oral administration of the β-alanine products A and D in Table 1 was evaluated according to a tingling sensation evaluation method, and an administration dosage, based on the β-alanine, is 22.8 mg/Kg (body weight).

TABLE 2

Administration evaluation on unsustained-release microencapsulated β-alanine

| | Administration evaluation | |
|---|---|---|
| Subject | Intensity | Description |
| Subject 1 | 7 | There was a slight prickle sensation in the hand for 15 minutes and a tingling sensation in the leg for 25 minutes, lasting for 1 h. |
| Subject 2 | 6 | There was a prickle sensation in the face, ears and back in 15 min, lasting for 45 min. |
| Subject 3 | 6 | There were prickle sensation and tingling sensation in the hands, face and ears in 10 min, lasting for 30 min. |

TABLE 3

Administration evaluation on sustained-release microencapsulated β-alanine product D

| Subject | Administration evaluation | |
|---|---|---|
| | Intensity | Description |
| Subject 1 | 1 | There was a tingling sensation in the hands in 10 min, lasting for 40 min. |
| Subject 2 | 1 | There was a tingling sensation in the shoulders in 1 h. |
| Subject 3 | 1 | There was no tingling sensation basically. |
| Subject 4 | 1 | There was tingling sensation in the legs in 45 min, lasting for 10 min. |
| Subject 5 | 1 | There was tingling sensation in the throat in 30 min, lasting for 40 min. |

Second Embodiment: Preparation and Characterization of Microencapsulated β-Alanine Product E 205 g hydrogenated palm oil was heated and melted, and 820 g β-alanine was placed in a fluidized bed and coated by a top spraying process. An inlet air temperature of the fluidized bed was 55° C., an air volume was 35 m³/h, an atomizing pressure was 0.3 MPa, a flow speed was 20 ml/min, an operation was conducted for 100 min, sustained-release β-alanine microcapsule powder E was acquired, a β-alanine content thereof was 80.1%, and a surface amino acid content was 9.2%. According to the release rate measurement method, the release rate in 0.1N hydrochloric acid solution and pH6.8 phosphate buffer was measured, and the result was shown in Table 4.

TABLE 4

50% release rate of sustained-release microencapsulated β-alanine

| Time | 0.1N hydrochloric acid solution | pH 6.8 phosphate buffer |
|---|---|---|
| 1 h | 2.7% | 15.0% |
| 2 h | 2.7% | 23.8% |
| 3 h | 4.0% | 25.5% |
| 4 h | 5.3% | 30.4% |
| 5 h | 6.7% | 33.9% |
| 6 h | 6.7% | 38.6% |

The result showed that: β-alanine was easy to be dissolved in water, and was quickly and completely released in 0.1N hydrochloric acid solution or pH6.8 phosphate buffer. After microencapsulation processing, the release rate of the β-alanine was obviously slowed; the release rate in 0.1N hydrochloric acid solution for stimulating gastric fluid was very little, the release rate in pH6.8 phosphate buffer for stimulating gastric fluid was accelerated, and the product causing abnormal sensation with different intensities could be acquired through adjusting the release rate.

Third Embodiment: Preparation and Characterization of Microencapsulated β-Alanine Product F The preparation method of the microencapsulated β-alanine was that: 700 g hydrogenated palm oil was heated and melted, and 1400 g β-alanine was placed in a fluidized bed and coated by a top spraying process. An inlet air temperature of the fluidized bed was 45° C., an air volume was 50 m³/h, an atomizing pressure was 0.2 MPa, a flow speed was 12 ml/min, an operation time was 120 min, β-alanine microcapsule powder F was acquired, a β-alanine content thereof was 66.6%, a surface amino acid content was 9.0%, a 6 h release rate was 38.2%, an 18 h release rate was 47.5%, and the evaluation intensity of a tingling sensation was 2 scores.

Fourth Embodiment: Preparation and Characterization of Microencapsulated β-Alanine Product G The preparation method of the microencapsulated β-alanine was that: 600 g hydrogenated palm oil and 12 g soybean phospholipid were heated and melted, and 1400 g β-alanine was placed in a fluidized bed and coated by a bottom spraying process. An inlet air temperature of the fluidized bed was 45° C., an air volume was 50 m³/h, an atomizing pressure was 0.3 MPa, a flow speed was 20 ml/min, an operation time was 120 min, β-alanine microcapsule powder G was acquired, a β-alanine content thereof was 70.5%, a surface amino acid content was 12.4%, a 6 h release rate was 88.7%, an 18 h release rate was 95.5%, and the evaluation intensity of a tingling sensation was 3 scores.

Fifth Embodiment: Preparation and Characterization of Microencapsulated β-Alanine Product H The preparation method of the microencapsulated β-alanine was that: 700 g hydrogenated palm oil, 21 g sunflower phospholipid and 10.5 g glycerol monolaurate were heated and melted, then suddenly cooled to 3° C., and reserved after keeping for 24 h, 1400 g β-alanine was dispersed in melted release material, and then was atomized, cooled and screened, β-alanine microcapsule powder H was acquired, a β-alanine content thereof was 65.9%, a surface amino acid content was 5.0%, a 6 h release rate was 71.4%, an 18 h release rate was 99.6%, and the evaluation intensity of a tingling sensation was 1 score.

Sixth Embodiment: Preparation and Characterization of Microencapsulated β-Alanine Product I The preparation method of the microencapsulated β-alanine was that: 480 g hydrogenated palm oil, 24 g sunflower phospholipid and 4.8 g glycerol monooleate were heated and melted, then suddenly cooled to 0° C., and reserved after keeping for 24 h, and then 1400 g β-alanine was placed in a fluidized bed and coated by a bottom spraying process. An inlet air temperature of the fluidized bed was 51° C., an air volume was 47 m³/h, an atomizing pressure was 0.2 MPa, a flow speed was 19 ml/min, an operation time was 120 min, β-alanine microcapsule powder I was acquired, a β-alanine content thereof was 73.3%, a surface amino acid content was 4.7%, a 6 h release rate was 73.7%, an 18 h release rate was 98.4%, and the evaluation intensity of a tingling sensation was 1 score.

Seventh Embodiment: Preparation and Characterization of Microencapsulated β-Alanine Product J The preparation method of the microencapsulated β-alanine was that: 600 g hydrogenated palm oil, 6 g powder sunflower phospholipid and 18 g glycerol monolaurate were heated and melted, then suddenly cooled to 0° C., and reserved after keeping for 24 h, and then 1246 g β-alanine was placed in a fluidized bed and coated by a top spraying process. An inlet air temperature of the fluidized bed was 57° C., an air volume was 45 m³/h, an atomizing pressure was 0.2 MPa, a flow speed was 15 ml/min, an operation time was 150 min, β-alanine microcapsule powder J was acquired, a β-alanine content thereof was 67.5%, a surface amino acid content was 4.5%, a 6 h release rate was 71.7%, an 18 h release rate was 97.0%, and the evaluation intensity of a tingling sensation was 1 score.

Eighth Embodiment: Preparation and Characterization of Microencapsulated β-Alanine Product K The preparation method of the microencapsulated β-alanine was that: 500 g hydrogenated palm oil, 100 g hydrogenated cottonseed oil, 36 g soybean phospholipid, and 2.4 g glycerol dilaurate were heated and melted, and 1400 g β-alanine was placed in a fluidized bed and coated by a bottom spraying process. An inlet air temperature of the fluidized bed was 62° C., an air volume was 45 m³/h, an atomizing pressure was 0.1 MPa, a flow speed was 10 ml/min, an operation time was 150 min, β-alanine microcapsule powder K was acquired, a β-alanine content thereof was 70.3%, a surface amino acid content was 5.4%, a 6 h release rate was 71.1%, an 18 h release rate was 96.5%, and the evaluation intensity of a tingling sensation was 1 score.

Ninth Embodiment: Preparation and Characterization of Microencapsulated β-Alanine Product L The preparation method of the microencapsulated β-alanine was that: 400 g hydrogenated palm oil, 200 g hydrogenated sunflower oil, 3 g powder sunflower phospholipid, and 30 g glycerol monopalmitate were heated and melted, and 1470 g β-alanine was placed in a fluidized bed and coated by a top spraying process. An inlet air temperature of the fluidized bed was 62° C., an air volume was 45 m³/h, an atomizing pressure was 0.1 MPa, a flow speed was 10 ml/min, an operation time was 150 min, β-alanine microcapsule powder L was acquired, a β-alanine content thereof was 70.9%, a surface amino acid content was 5.4%, a 6 h release rate was 70.1%, an 18 h release rate was 95.9%, and the evaluation intensity of a tingling sensation was 1.5 scores.

Tenth Embodiment: Preparation and Characterization of Microencapsulated β-Alanine Product M The preparation method of the microencapsulated β-alanine was that: 450 g hydrogenated palm oil, 150 g hydrogenated soybean oil, 3 g glycerol dioleate, and 1400 g β-alanine were mixed, then heated to 45° C., and stirred by a rotate speed of 2000 RPM, the melted release material was evenly coated on the surface of the β-alanine with stirring, an operation time was 60 min, β-alanine microcapsule powder M was acquired, a β-alanine content thereof was 70.8%, a surface amino acid content thereof was 2.8%, a 6 h release rate thereof was 18.7%, an 18 h release rate was 23.9%, and the evaluation intensity of a tingling sensation was 0 score.

Eleventh Embodiment: Preparation and Characterization of Microencapsulated β-Alanine Product N The preparation method of the microencapsulated β-alanine was that: 390 g hydrogenated palm oil, 210 g hydrogenated cottonseed oil, 60 g concentrated phospholipid, 1.2 g glycerol monopalmitate, and 1540 g β-alanine were mixed, then heated to 73° C., and stirred by a rotate speed of 1000 RPM, the melted release material was evenly coated on the surface of the β-alanine with stirring, an operation time was 50 min, β-alanine microcapsule powder N was acquired, a β-alanine content thereof was 71.7%, a surface amino acid content thereof was 5.5%, a 6 h release rate thereof was 65.6%, an 18 h release rate was 91.7%, and the evaluation intensity of a tingling sensation was 1.5 scores.

Twelfth Embodiment: Preparation and Characterization of Microencapsulated β-Alanine Product P The preparation method of the microencapsulated β-alanine was that: 600 g hydrogenated peanut oil, 0.6 g sunflower phospholipid and 60 g glycerol dilaurate were heated and melted, and 1540 g β-alanine was placed in a fluidized bed and coated by a bottom spraying process. An inlet air temperature of the fluidized bed was 73° C., an air volume was 20 m³/h, an atomizing pressure was 0.1 MPa, a flow speed was 3 ml/min, an operation time was 150 min, β-alanine microcapsule powder P was acquired, a β-alanine content thereof was 70.6%, a surface amino acid content thereof was 19.7%, a 4 h release rate thereof was 100%, and the evaluation intensity of a tingling sensation was 6 scores.

The product release data of the microencapsulated β-alanine product prepared according to second to twelfth embodiments above in 18 h is shown in Table 5, and it can be seen from Table 5 that:

TABLE 5

| No. | Tingling evaluation | Surface active ingredient content | Release rate (pH 6.8 phosphate buffer) | | | | | | |
|-----|---------------------|-----------------------------------|----|----|----|----|----|----|-----|
| | | | 1 h | 2 h | 3 h | 4 h | 5 h | 6 h | 18 h |
| E | | 9.2% | 15.0% | 23.8% | 25.5% | 30.4% | 33.9% | 38.6% | |
| F | 2 | 9.0% | 15.2% | 23.8% | 30.1% | 35.2% | 36.9% | 38.2% | 47.5% |
| G | 3 | 12.4% | 38.3% | 54.9% | 65.8% | 77.1% | 82.2% | 88.7% | 95.5% |
| H | 1 | 5.0% | 26.0% | 38.9% | 45.1% | 55.3% | 62.3% | 71.4% | 99.6% |
| I | 1 | 4.7% | 27.1% | 37.2% | 43.5% | 56.4% | 62.9% | 73.7% | 98.4% |
| J | 1 | 4.5% | 25.2% | 36.2% | 45.5% | 54.7% | 62.3% | 71.7% | 97.0% |
| K | 1 | 5.4% | 27.5% | 36.6% | 44.3% | 55.9% | 62.1% | 71.1% | 96.5% |
| L | 1.5 | 5.4% | 28.6% | 38.1% | 44.9% | 55.0% | 61.6% | 70.1% | 95.9% |
| M | 0 | 2.8% | 7.8% | 8.5% | 10.9% | 13.0% | 13.9% | 18.7% | 23.9% |
| N | 1.5 | 5.5% | 29.0% | 40.0% | 44.9% | 48.5% | 56.4% | 65.6% | 91.7% |
| P | 6 | 19.7% | 38.2% | 65.5% | 97.3% | 100% | — | — | — |

In the tingling evaluation experiment in Table 5, the dosage of the subject was 45.7 mg/kg (body weight).

It can be seen from Table 5 that, the adding of the fatty glyceride can promote the encapsulation promotion efficiency of the microencapsulated β-alanine in the present invention; moreover, the using of the phospholipid promotes the release of the core material in the microencapsulated β-alanine in the present invention; the fatty glyceride and the phospholipid are added according to the limited ratio of the present invention, then the relationship between the encapsulation and the release of the microencapsulated β-alanine product in the present invention is balanced, and release kinetics of the product is effectively optimized, so that the release of the product is stable, and effective encapsulation and sustained release with constant speed are realized.

The invention claimed is:

1. A microencapsulated β-alanine using β-alanine as a core material and a mixture of a wall material and an additive as a release material, wherein:
   the additive comprises a fatty acid-based saturated or unsaturated fatty glyceride containing 12 to 22 carbon atoms and a phospholipid,
   the fatty glyceride is a monoglyceride, a diglyceride, or a mixture thereof in any ratio,
   a dosage of the fatty glyceride is 0.2 to 5% of a mass of the wall material; and
   a dosage of the phospholipid is 0.5 to 10% of a mass of the wall material.

2. The microencapsulated β-alanine according to claim 1, wherein the fatty glyceride is a fatty acid-based fatty glyceride containing 16 to 18 carbon atoms.

3. The microencapsulated β-alanine according to claim 2, wherein the fatty glyceride comprises a compound selected from the group consisting of glyceryl hexadecanoate, glyceryl hexadecenoate, glyceryl octadecanoate, glycerol octadecenoate, glyceryl octadecadienoate, and glyceryl octadecatrienoate.

4. The microencapsulated β-alanine according to claim 1, wherein a mass ratio of the fatty glyceride to the phospholipid is 1:50 to 10:1.

5. The microencapsulated β-alanine according to claim 1, wherein the wall material is selected from the group consisting of hydrogenated palm oil, hydrogenated soybean oil, hydrogenated sunflower oil, hydrogenated peanut oil, hydrogenated cottonseed oil, hydrogenated corn oil, stearic acid, beewax, carnauba wax, and a mixture thereof in any ratio.

6. The microencapsulated β-alanine according to claim 5, wherein the wall material is selected from the group consisting of hydrogenated palm oil, hydrogenated soybean oil, hydrogenated sunflower oil, hydrogenated peanut oil, hydrogenated cottonseed oil, hydrogenated corn oil, and a mixture thereof in any ratio.

7. The microencapsulated β-alanine according to claim 6, wherein the wall material is hydrogenated palm oil.

8. The microencapsulated β-alanine according to claim 7, wherein a mass ratio of the wall material to the β-alanine is 1:1 to 19.

9. The microencapsulated β-alanine according to claim 6, wherein a mass ratio of the wall material to the β-alanine is 1:1 to 19.

10. The microencapsulated β-alanine according to claim 1, wherein a surface amino acid content thereof is less than 10%; and a release rate in a pH 6.8 phosphate buffer is no more than 50% at 1 h, and the microencapsulated β-alanine is completely released at 18 h.

11. A preparation method of the microencapsulated β-alanine according to claim 1, comprising a step of preparing release materials: melting the wall material, stirring at a hot-melting temperature, adding the additive and mixing evenly, cooling an acquired mixture to a temperature of 0 to 5° C., and using the mixture as the release material after being placed at 0 to 5° C. for at least 24 h.

* * * * *